United States Patent [19]

Curran et al.

[11] 4,085,108

[45] Apr. 18, 1978

[54] SILICON DERIVATIVES OF TETRAHYDROQUINOLINES

[75] Inventors: Adrian Charles Ward Curran, North Humberside; Robin Gerald Shepherd, Maidenhead, both of England

[73] Assignee: John Wyeth & Brother Ltd., Taplow, England

[21] Appl. No.: 721,263

[22] Filed: Sep. 8, 1976

Related U.S. Application Data

[63] Continuation-in-part of Ser. No. 526,565, Nov. 25, 1974, Pat. No. 4,000,142.

[30] Foreign Application Priority Data

Dec. 17, 1973 United Kingdom ............... 58307/73
Feb. 4, 1974 United Kingdom ................. 4956/74
Mar. 27, 1974 United Kingdom ............... 13514/74
Jul. 12, 1974 United Kingdom ............... 30934/74

[51] Int. Cl.$^2$ .......................................... C07D 215/12
[52] U.S. Cl. ............................................. 260/283 SC
[58] Field of Search ................................. 260/283 SC

[56] References Cited

U.S. PATENT DOCUMENTS 4,000,142  12/1976  Curran et al. ................. 260/283 SC Primary Examiner—Nicholas S. Rizzo
Attorney, Agent, or Firm—Arthur E. Wilfond

[57] ABSTRACT

The invention relates to novel silicon derivatives of tetrahydroquinolines, which are intermediates in a process for preparing 5,6,7,8-tetrahydroquinoline-8-carboxamides and thiocarboxamides.

3 Claims, No Drawings

SILICON DERIVATIVES OF TETRAHYDROQUINOLINES

The present application is a continuation-in-part of Ser. No. 526,565, now U.S. Pat. No. 4,000,142.

The invention relates to novel silicon derivatives of tetrahydroquinolines which are intermediates in a new process for preparing tetrahydroquinoline derivatives which is described in our copending application Ser. No. 526,565 filed 25 Nov., 1974.

The present invention provides a compound of formula III

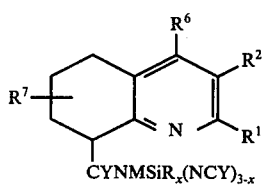

wherein $R^1$, $R^2$ and $R^6$ are independently hydrogen, trifluoromethyl, alkyl of 1 to 6 carbon atoms, phenyl alkyl of 7 to 12 carbon atoms or phenyl, or $R^1$ and $R^2$ taken together represent an $R^7$ substituted alkylene chain, said alkylene chain consisting of 3 to 5 carbon atoms, inclusive; $R^7$ is hydrogen, alkyl of 1 to 6 carbon atoms, gem-di-n-alkyl in which each alkyl group has 1 to 6 carbon atoms, phenyl alkyl of 7 to 12 carbon atoms or phenyl; with the proviso that when $R^1$ and $R^2$ or $R^2$ and $R^6$ are both alkyl, they are normal or secondary alkyl; Y is oxygen or sulphur, M is sodium, potassium, lithium, MgCl, MgBr or MgI; each group R is independently alkyl of 1 to 6 carbon atoms, phenyl or phenyl alkyl of 7 to 12 carbon atoms, x is an integer from 0 to 3 inclusive.

Also provided by this invention is a compound of formula (IV)

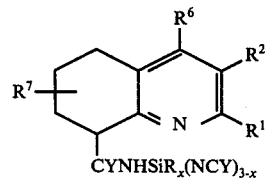

wherein $R^1$, $R^2$, $R^6$, $R^7$, Y, R and x are as defined above.

When any of $R^1$, $R^2$, $R^6$ or $R^7$ is an alkyl radical this is a lower alkyl radical which may be a straight or branched chain, having from 1 to 6 carbon atoms, e.g. methyl, ethyl, n-, and iso-propyl and n-, s- and t- butyl, $R^7$ may be a gem dimethyl group and when a single radical may be on the same carbon atom as the silicon-containing group. The term alkyl radical is also intended to embrace cyclic alkyl radicals e.g. cyclobutyl, cyclopentyl and cyclohexyl. When any of $R^1$, $R^2$, $R^6$ or $R^7$ is a phenylalkyl radical, the lower alkyl portion may be as discussed above for a lower alkyl radical.

Particularly preferred compounds are bicyclic compounds especially those in which one of $R^1$, $R^2$ and $R^6$ is methyl, the others are hydrogen and $R^7$ is hydrogen. Tricyclic compounds may be symmetrical (i.e. $R^1$ and $R^2$ are joined to form an alkylene chain of 4 carbon atoms) or unsymmetrical i.e. $R^1$ and $R^2$ are joined to form an alkylene chain of 3 or 5 carbon atoms.

The compounds of formula (III) and (IV) are intermediates in a process for preparing compounds of formula I

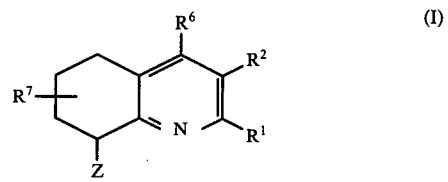

and acid addition salts thereof, wherein Z is $CONH_2$, $CSNH_2$ or CN, $R^1$, $R^2$, $R^6$ and $R^7$ are as defined in connection with formulae (III) and (IV), which process comprises treating a compound of formula II

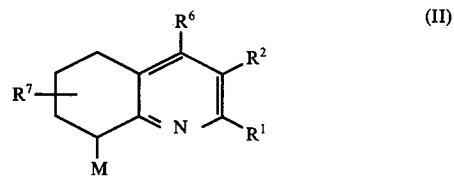

wherein $R^1$, $R^2$, $R^6$ and $R^7$ are as defined in connection with formula I above and M is sodium, potassium, lithium or MgHal where Hal is chlorine, bromine or iodine, with a silyl compound of formula $R_xSi(NCY)_{4-x}$ wherein R and Y are as defined in connection with formula III, and x has a value from 0 to 3 then subjecting the product to hydrolysis or alcoholysis, with the proviso that when a compound of formula I in which Z is CN is desired the molar ratio of compound $R_xSi(NCY)_{4-x}$ to compound IIa is at least 2:1 and x is 3 and Y is S.

Compounds of formula I in which Z is $CSNH_2$ or CN display pharmacological activity, namely anti-ulcer and/or anti-secretory activity. Compounds where Z is $CONH_2$ are intermediates for the corresponding compounds in which Z is $CSNH_2$ or CN. The tests for the pharmacological activity may be carried out by the method of Brodie & Hanson, J. Applied Physiology, 5, 291 (1960) or Gastroenterology 38, 353 (1960) and the method of H. Shay, D. Sun and H. Greenstein, Gastroenterology 26, 906–913, (1954).

Examples of the compound $R_xSi(NCY)_{4-x}$ are:

| | |
|---|---|
| x = 0 | $Si(NCY)_4$ |
| x = 1 | $RSi(NCY)_3$ |
| x = 2 | $R_2Si(NCY)_2$ |
| x = 3 | $R_3SiNCY$ | wherein R has any of the meanings given above.

When x is 3 the residue $R_xSi$ may be a tri-alkyl-, tri-phenyl- or tri-phenylalkyl-silyl group and is preferably a tri-lower alkyl silyl group, e.g. trimethylsilyl.

The reaction with the compound of formula $R_xSi(NCY)_{4-x}$ is conducted under anhydrous conditions, preferably in an inert solvent, for example a hydrocarbon solvent such as benzene, toluene or hexane. Ethers including cyclic ethers such as tetrahydrofuran should be avoided. Conveniently the starting material of formula II is prepared in situ and the same solvent is used for the reaction with the compound of formula $R_xSi(NCY)_{4-x}$. However where a compound of formula II wherein M is MgHal is used these are usually prepared in ether as solvent. The ether is removed and the reaction with the silicon compound is conducted in a different solvent.

The product of the first stage is a compound of formula III

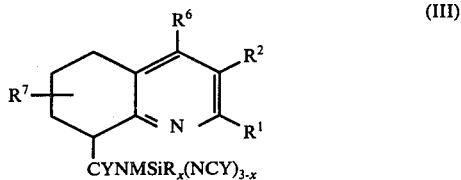

(wherein $R^1$, $R^2$, $R^6$, $R^7$, Y, M, R and $x$ are as defined above) which is converted by water or alcohol to the desired compound of formula I, via an intermediate of formula IV which may be transient

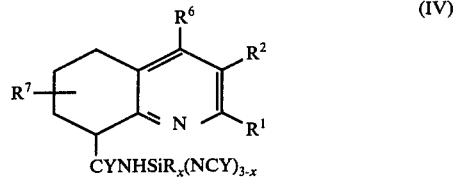

wherein R is the organic residue above and Y is oxygen or sulphur and M, $R^1$, $R^2$, $R^6$, $R^7$, $m$ and $x$ are as defined in connection with formula III above. However, it has been shown that a compound of formula IV wherein R is phenyl and $x$ is 3 can be isolated and hydrolysed to the corresponding compound of formula I.

Compounds of formula III and IV constitute the present invention and the process for preparing them described above. These compounds are not isolated but are obtained and used in solution.

The desired compound of formula I wherein Z is $CONH_2$, or $CSNH_2$ is conveniently formed by treating a compound of formula III with water or a lower alcohol, e.g. ethanol.

The starting materials of formula II wherein M is sodium, potassium or lithium are described in German Offenlegungsschrift No. 2,352,585 or may be prepared by analogous methods. They may be prepared by reacting a compound of formula I wherein Z is hydrogen with a metal organic compound e.g $MR^{10}$ wherein M is sodium, potassium or lithium and $R^{10}$ is alkyl, phenyl or phenyl-alkyl.

It has been found that when a compound of formula I in which $R^1$ is methyl and $R^2$, $R^6$ and $R^7$ are hydrogen and M is hydrogen is treated with metal alkyl the metal atom may be inserted either at the desired position or in the methyl group $R^1$. This side reaction may also occur with any compound containing an alkyl group $R^1$ in which there are one or two hydrogen atoms on the carbon atom adjacent to the pyridine ring. These by-products which contain a metal atom in an alkyl group $R^1$ do not normally react with, alkyl-silyl isothiocyanates.

Compounds of formula II where M is MgHal may be prepared by treating a compound of formula I wherein Z is hydrogen with an alkyl magnesium halide $R^{11}$MgHal wherein $R^{11}$ is an alkyl group, preferably a lower alkyl group, and Hal is chlorine, bromine or iodine. $R^{11}$ may be a straight or branched chain alkyl group being preferred. Conveniently the compound of formula II is prepared in situ. If ether is used as a solvent this is distilled off and another solvent added after which the product is then treated with the compound of formula $R_xSi(NCY)_{4-x}$, followed by hydrolysis or alcoholysis to obtain the desired compound of formula I.

We have found that by conducting the above reaction with a compound (II) and a compound of formula $R_3SiNCS$ wherein the molar ratio exceeds 2:1 a compound of formula I wherein Z is cyano is obtained in addition to the compound of formula I wherein Z is $CSNH_2$.

For the preparation of compounds where Z is $CSNH_2$ or $CONH_2$ it is preferred that the ratio of the silyl compound to the compound of formula II is in the range 0.5:1 to 2:1, e.g. 0.5:1 to 1.5.

With higher ratios e.g. 4:1 the cyano compound has been obtained exclusively in certain instances.

Accordingly a process for preparing a compound of formula I as defined above wherein Z is cyano comprises treating a compound of formula (II) as defined above with a compound of formula $R_3SiNCS$ in at least 2:1 molar ratio, wherein R is an alkyl, aryl or aralkyl residue or $R_x$ is any mixture of these and subjecting the product to hydrolysis or alcoholysis.

We have also found that yields of the final product of formula I wherein Z is $CONH_2$ or $CSNH_2$ may be improved if the reaction with the metal alkyl is conducted in the presence of a secondary amine (preferably in a molar amount equal to that of the metal alkyl) and then followed by reaction with the silyl isothiocyanate or isocyanate. This may be achieved conveniently by preparing the starting material of formula II wherein M is lithium sodium or potassium in situ by reaction of a compound of formula II wherein M is hydrogen with a metal amide derived from a secondary amine.

The metal amide may be formed in situ by reacting a metal $MR^{10}$ wherein M is sodium, potassium or lithium and $R^{10}$ is alkyl, aryl, or aralkyl with a secondary amine, (preferably in a molar amount equal to that of the metal alkyl). The compound of formula I wherein X is hydrogen may then be added.

Preferably the metal M is lithium. The secondary amine may be a dialkylamine e.g. diethylamine, di-isopropylamine, di-tertiarybutyl amine, di-n-decylamine, dicyclohexylamine, N-tertiaryamyl-N-t-butylamine, N-isopropyl-N-cyclohexylamine, or N(1'-ethylcyclohexyl)-1,1,3,3,tetramethylbutylamine or a cyclic compound e.g. piperidine, or 2,2,6,6-tetramethylpiperidine.

The following examples illustrate the invention. Temperatures are in ° C.

EXAMPLE 1

3-Methyl-5,6,7,8-tetrahydroquinoline-8-thiocarboxamide

A solution of 3-methyl-5,6,7,8-tetrahydroquinoline (7.3 g., 0.05 mol.) in hexane (50 ml.) was cooled to 0° C and treated dropwise with stirring with a 15% w/w solution of butyl lithium in hexane (26 ml., 0.06 mol.) in an atmosphere of nitrogen. The reaction mixture was stirred at 0° C for an additional 1 hour and was added portionwise to a solution of trimethylsilylisothiocyanate (13.1 g., 0.1 ml.) in hexane (50 ml.) and under nitrogen keeping the internal temperature at −20° C. The reaction mixture was stirred for an additional 30 minutes at −20° C, allowed to warm to room temperature giving a solution of 3-methyl-5,6,7,8-tetrahydroquinoline-8-(N-lithio-N-trimethyl silyl)thiocarboxamide, and diluted with water (50 ml.) causing hydrolysis to 3-methyl-5,6,7,8-tetrahydroquinoline-8-(N-trimethylsilyl)thiocarboxamide which hydrolysed to the title compound. The pH was adjusted to 2.0 with conc. HCl and the hexane layer separated and discarded. The aqueous solution was adjusted to pH 10.0 with sodium carbonate and extracted with ethyl acetate (3 × 50 ml.). The combined extracts were dried (MgSO$_4$) and the solvent removed in vacuo. The residue was triturated with n-hexane and solid filtered and recrystallised from benzene to give the title compound as colourless needles (3.5 g., 39%) m.p. 153° identical in all respects to authentic material. (Found: C, 64.6; H, 7.0; N, 13.9%. C$_{11}$H$_{14}$N$_2$S requires: C, 64.1; H, 6.8; N, 13.6%). The hexane soluble material was distilled to give recovered 3-methyl-5,6,7,8-tetrahydroquinoline (3.5 g., 50%) b.p. 120°/15 mm.

EXAMPLE 2

3-Methyl-5,6,7,8-tetrahydroquinoline-8-carboxamide

A solution of 3-methyl-5,6,7,8-tetrahydroquinoline (7.3 g., 0.05 mol.) in hexane (50 ml.) was cooled to 0° C and treated dropwise with 15% w/w butyllithium in hexane (26 ml., 0.06 mol.) in a nitrogen atmosphere. The reaction mixture was allowed to stand at 0° C for 1 hour and was then added dropwise over 30 minutes to a solution of trimethylsilylisocyanate (19.5 g., 0.17 mol.) in hexane (50 ml.) keeping the internal temperature at −20° C. The reaction mixture was allowed to stand at −20° C for 1 hour, giving a solution of 3-methyl-5,6,7,8-tetrahydroquinoline-8-(N-lithio-N-trimethylsilyl)thiocarboxamide, and was then diluted with water (50 ml.) causing hydrolysis to 3-methyl-5,6,7,8-tetrahydroquinoline-8-(N-trimethylsilyl)thiocarboxamide and subsequent hydrolysis to the title compound. The pH was adjusted to 2.0 with conc. HCl. The hexane layer was separated and discarded and the aqueous solution adjusted to pH 10.0 with sodium carbonate and extracted with chloroform (3 × 25 ml.). The combined extracts were washed with saturated brine, dried and the solvent removed in vacuo. The residue was triturated with n-hexane, filtered and the solid crystallised from ethyl acetate to give the title compound as colourless needles (3.1 g., 35%) m.p. 104° C. identical in all respects to the authentic material (when crystallised from ethyl acetate). Analysis: Found C, 69.1; H, 7.4; N, 14.7. C$_{11}$H$_{14}$N$_2$O requires C, 69.5; H, 7.4; N, 14.7. The hexane soluble material was distilled to give recovered 3-methyl-5,6,7,8-tetrahydroquinoline (4.2 g.) b.p. 120°/15 mm.

EXAMPLE 3

8-Cyano-3-methyl-5,6,7,8-tetrahydroquinoline

A solution of 3-methyl-5,6,7,8-tetrahydroquinoline (29 g., 0.2 mol) in benzene (200 ml.) was cooled to 0° C and treated dropwise with a 15% w/w solution of n-butyl lithium in hexane (88 ml., 0.2 mol) under nitrogen. After 1 hour at 0° C the reaction mixture was added portionwise to a solution of trimethylsilylisocyanate (112 ml., 0.8 mol.) in benzene (200 ml.) at 0° C and under nitrogen. After 2½ hours at room temperature the reaction mixture was treated with water (100 ml.) and with 2N HCl to pH 2.0. The aqueous layer was separated, washed with ethyl acetate (1 × 50 ml.) and the pH adjusted to 9.0 with sodium carbonate and extracted with chloroform (3 × 100 ml.) The combined chloroform extracts were dried (MgSO$_4$) and the solvent removed in vacuo to give a red oil which was distilled first at 0.25 mmHg to give recovered 3-methyl-5,6,7,8-tetrahydroquinoline (17 g., 59%) b.p. 54°−7° and then at 0.05 mmHg to give the title compound as a pale red oil (12 g. 35%) b.p. 115°−20° R$_T$= 4.1/4 min. (3% SE30, 200° C) identical to authentic material.

EXAMPLE 4

4-Methyl-5,6,7,8-tetrahydroquinoline-8-thiocarboxamide

A solution of 4-methyl-5,6,7,8-tetrahydroquinoline (5.83 g., 0.04 mole) in dry benzene (40 ml.) was cooled to 0° and to the stirred solution was added dropwise a 15% w/w solution of butyl lithium in hexane (17.5 ml., 0.04 mole) under an atmosphere of nitrogen. The red reaction mixture was stirred at 0° for a further 30 minutes. Trimethylsilylisothiocyanate (5.6 ml., 0.04 mole) was then added dropwise, maintaining the temperature at 0°. After an additional 30 minutes, the solution of 4-methyl-5,6,7,8-tetrahydroquinoline-8-(N-lithio-N-trimethylsilyl)thiocarboxamide was allowed to warm to room temperature and diluted with water (40 ml.) causing hydrolysis to 4-methyl-5,6,7,8-tetrahydroquinoline-8-(N-trimethylsilyl) thiocarboxamide and subsequent hydrolysis to the title compound. The pH was adjusted to 2.0 by addition of conc. HCl and the benzene layer separated and discarded. The aqueous phase was adjusted to pH 10.0 by adding anhydrous Na$_2$CO$_3$ and extracted with CHCl$_3$ (3 × 40 ml.). The CHCl$_3$ solution was then dried (MgSO$_4$), filtered and evaporated (reduced pressure) to afford an oil (5.77 g.). Addition of ether caused crystallisation of the title compound as colourless needles. Filtration afforded 0.69 g. of base which was converted to the hydrochloride by dissolving in a minimum of EtOH, adding EtOH/HCl until just acid followed by ether to induce crystallisation. Filtration provided the title compound hydrochloride as colourless needles, (0.64 g.), m.p. 213° C. Analysis: Found: C, 54.95; H, 6.40; N, 11.52. C$_{11}$H$_{14}$N$_2$S.HCl requires C, 54.42; H, 6.23; N, 11.54%.

EXAMPLE 5

3,7,7-Trimethyl-5,6,7,8-tetrahydroquinoline-8-thiocarboxamide hydrochloride

A solution of 3,7,7-trimethyl-5,6,7,8-tetrahydroquinoline (10.3 g. 59 m. mole) in hexane (50 ml.) was cooled to 0° C and treated dropwise with 1 15% w/w solution of butyl lithium in hexane (25.8 ml. 59 m. mole) and allowed to stand at 0° C for 1 hour. The solution was treated dropwise with trimethylsilylisothiocyanate (8.25 ml., 59 m. mole) in hexane (50 ml.) and allowed to stand at 0° C for 1½ hour. The solution of 3,7,7-trimethyl-5,6,7,8-tetrahydroquinoline-8-(N-lithio-N-trimethylsilyl)thiocarboxamide was warmed to room temperature diluted with water (25 ml.) causing hydrolysis to 3,7,7,trimethyl-5,6,7,8-tetrahydroquinoline-8-(-N-trimethylsilyl)thiocarboxamide and subsequent hydrolysis to the title compound, and the pH adjusted to 1.0 with conc. HCl. The solution was extracted with ether (3 × 25 ml.) and the aqueous phase adjusted to pH 10.0 with sodium carbonate and extracted with chloroform (3 × 50 ml.). The combined extracts were washed with brine, dried (MgSO$_4$) and the solvent removed. The residual oil (12.6 g.) was chromatographed on silica gel and eluted with methanol-chloroform. Recovered 3,7,7-trimethyl-5,6,7,8-tetrahydroquinoline (7.6 g.) was obtained by elution with 2% methanol-chloroform. Elution with 5% methanolchloroform. Elution with 5% methanol-chloroform gave 3,7,7-trimethyl-5,6,7,8-tetrahydroquinoline-8-thiocarboxamide (2 g., 15%) as a yellow solid which was recrystallised from benzene-hexane as pale yellow needles and converted to the hydrochloride by dissolving in ether and treating with an excess of dry HCl. The resultant solid was recrystallised from isopropyl alcohol to give the one and a quarter hydrate of the title compound as colourless needles m.p. 162° C. (Found: C, 53.3; H, 7.35; N, 9.5. $C_{13}H_{18}N_2S.HCl. 1.1/4H_2O$ requires: C, 53.3; H, 7.4; N, 9.55%).

EXAMPLE 6

3-Methyl-5,6,7,8-tetrahydroquinoline-8-thiocarboxamide

Following the general procedure of Example 1 but using different molar ratios of trimethylsilylisothiocyanate (TMS.NCS): 8-Lithio-3-methyl-5,6,7,8-tetrahydroquinoline (LiTHQ) (prepared from equimolar amounts of butyl lithium and 3-methyl-5,6,7,8-tetrahydroquinoline) the following results were obtained.

| MOlar Ratio* TMSNCS:LiTHO | Yield** i.e. %THQ converted to title product | Yield as % TMS-NCS converted to title product |
|---|---|---|
| 0.5:1 | 35 | 70 |
| 0.8:1 | 34 | 42 |
| 1:1 | 30–40 | 30–40 |
| 1.2:1 | 36 | 30 |
| 1.5:1 | 39 | 26 |
| 2:1 | 30*** | 15*** |

*solvent benzene
**quantitative recovery of unconverted 3-methyl-5,6,7,8-tetrahydroquinoline(THQ)
***8-nitrile (10%) also obtained

EXAMPLE 7

3-Methyl-5,6,7,8-tetrahydroquinoline-8-thiocarboxamide

3-Methyl-5,6,7,8-tetrahydroquinoline (7.3 g, 0.05 mol.) was added to a solution of isopropylmagnesium bromide [prepared from isopropylbromide (6.15 g, 0.05 mol), magnesium (1.44 g, 0.06 mol) in ether (10 ml.)] and the solution heated at 60° to remove the ether by distillation. Toluene (5 ml.) was added and the reaction mixture was heated at 120° for 2 hours, cooled, diluted with toluene (30 ml) and this solution was added to a solution of trimethylsilyl isothiocyanate (7.85 g, 0.06 mol) in toluene (50 ml.) at 0° C. The reaction mixture was stirred at room temperature for 12 hours. The solution of 3-methyl-5,6,7,8-tetrahydroquinoline-8-(N-bromomagnesio-N-trimethylsilyl)thiocarboxamide was diluted with water (15 ml.) causing hydrolysis to 3-methyl-5,6,7,8-tetrahydroquinoline-8-(N-trimethylsilyl) thiocarboxamide and subsequent hydrolysis to the title compound and the pH adjusted to 2.0 with Conc. HCl. The aqueous solution was extracted with ether and the extracts discarded. The aqueous solution was adjusted to pH 9.0 with $Na_2CO_3$ and extracted with chloroform (3 × 50 ml.). The combined extracts were washed with brine, dried and the solvent removed to give a mixture of 3-methyl-5,6,7,8-tetrahydroquinoline and the title compound (5%) which was isolated by chromatography and identified by comparison with authentic material.

EXAMPLE 8

2,3,5,6,7,8-Hexahydro-1H-cyclopenta[b]-quinoline-5-thiocarboxamide 2-(2'-Oxocyclopentyl)methyl cyclohexanone was prepared from 2-(dimethylaminomethyl)cyclohexanone and cyclopentanone according to the method described in Ann. Chim. 1963, 53 (6), 819 and was isolated as a colourless oil in 80% yield b.p. 92°/0.05 mm.

2,3,5,6,7,8-hexahydro-1H-cyclopenta[b]-quinoline was prepared from 2-(2'-oxocyclopentyl)methylcyclohexanone according to the method described in Ann. Chim., 1963, 53 (6), 819 and was isolated in 65% yield as a colourless oil b.p. 80°/0.05 mm. The hydrochloride was prepared for characterisation by treating an ethereal solution of the base with ethereal HCl and was isolated as the hemihydrate as colourless needles from ethanol-ether. m.p. 104° C. (Found: C, 65.7, H, 7.8; N, 6.6. $C_{12}H_{16}N.HCl. \frac{1}{2}HO$ requires: C, 65.8; H, 7.8; N, 6.4%.)

A solution of 2,3,5,6,7,8-hexahydro-1H-cyclopenta[b]quinoline(5.19g., 0.03 mol.) in benzene (5 ml.) was cooled to 0° C and treated with a 15% w/w solution of butyl lithium in hexane (13.5 ml., 0.03 mol.) and allowed to stand at 0° C for 1 hour.

The reaction mixture was treated dropwise with a solution of trimethylsilylisothiocyanate (4.5 ml., 0.03 mol.) in benzene (2 ml.) with cooling in ice. The reaction mixture was stirred at 0° C for an additional 1 hour. The solution of 2,3,5,6,7,8-hexahydro-1H-cyclopenta[b]quinoline-5-(N-lithio-N-trimethylsilyl)thiocarboxamide was diluted with water (15 ml.), causing hydrolysis to 2,3,5,6,7,8-hexahydro-1H-cyclopenta[b]quinoline-5-(N-trimethylsilyl)thiocarboxamide and subsequent hydrolysis to the title compound, and the pH adjusted to 2.0 with 2N HCl. The solution was extracted with ethyl acetate (3 × 50 ml.) and the extracts discarded. The aqueous solution was adjusted to pH 9.0 with $Na_2CO_3$ and extracted with chloroform (3 × 50 ml.).

The combined extracts were washed with brine, dried ($MgSO_4$) and the solvent removed in vacuo. The residual oil was diluted with n-hexane (100 ml.) and cooled to 0° C. The precipitated solid was filtered, recrystallised from isopropanol, dissolved in ether and treated with excess ethereal HCl. The resultant solid was recrystallised from ethanol-ether to give the hydrochloride monohydrate of the title compound (0.9g) m.p. 118° C (Found: C, 54.6; H, 6.3; N, 10.0. $C_{13}H_{16}N_2S.HCl. H_2O$ requires: C, 54.5; H, 6.6; N, 9.8%).

EXAMPLE 9

3-Methyl-5,6,7,8-tetrahydroquinoline-8-thiocarboxamide

A solution of di-isopropylamine [11.11 g., 0.11 mol.) in benzene (50 ml.) was cooled to 0° C and treated portionwise with a 9% w/v solution of butyl lithium in hexane (79 ml., 0.11 mol.). After 45 minutes at 0° C the solution was treated dropwise with 3-methyl-5,6,7,8-tetrahydroquinoline (14.7 g., 0.10 mol.) with rapid stirring and under an atmosphere of nitrogen. After 1½ hours at 0° C the red suspension was treated portionwise over 2 minutes with trimethylsilylisothiocyanate (14.7 ml., 0.11 mol.) and the reaction mixture stirred at 0° C for ½ hour and at room temperature for 1 hour. The solution of 3-methyl-5,6,7,8-tetrahydroquinoline-8-(N-lithio-N-trimethylsilyl)thiocarboxamide was diluted with water (25 ml.), causing hydrolysis to 3-methyl-5,6,7,8-tetrahydroquinoline-8-(N-trimethylsilyl)thiocarboxamide and subsequent hydrolysis to the title compound and the pH adjusted to 2.0 with 2N HCl. The mixture was extracted with ethylacetate (3 × 25 ml.) and the combined extracts discarded. The aqueous solution was adjusted to pH 10.0 with sodium carbonate and extracted with chloroform (3 × 50 ml.). The combined extracts were washed with saturated brine (1 × 50 ml.), dried (MgSO$_4$) and the solvent removed in vacuo. The residual oily solid was triturated with n-hexane (100 ml.) and the solid filtered and recrystallised from isopropanol to give the title compound as pale yellow needles (8.9 g., 43%) m.p. 153° C identical in all respects to authentic material. The filtrate was analysed by g.l.c. (10% SE30, T=160° C and identified as a mixture of 8-cyano-3-methyl-5,6,7,8-tetrahydroquinoline (1 g., 6% yield based on starting material) and recovered 3-methyl-5,6,7,8-tetrahydroquinoline (7.17 g., 48% yield based on starting material)

EXAMPLE 10

5,6,7,8-Tetrahydroquinoline-8-thiocarboxamide

A solution of di-isopropylamine (33.3g, 0.33 mol) in benzene (150 ml) was cooled in ice and treated with 9% w/v butyl-lithium in hexane (237 ml, 0.33 mol). After 45 minutes the solution was treated with 5,6,7,8-tetrahydroquinoline (39.9 g, 0.3 mol) dropwise with stirring. After 1.5 hours trimethylsilyl-isothiocyanate (43.2 ml. 0.3 mol) was added and the resulting solution was allowed to stand at 0° C for 0.5 hours and at room temperature for 1 hour. Water (50 ml.) was added to the solution of 5,6,7,8-tetrahydroquinoline-8-(N-lithio-N-trimethylsilyl) thiocarboxamide causing hydrolysis to 5,6,7,8-tetrahydroquinoline-8-(N-trimethylsilyl)thiocarboxamide and subsequent hydrolysis to the title compound, and the resulting mixture acidified with 2N HCl. The acid solution was separated, washed with ethyl acetate and the pH was adjusted to 9 with solid sodium carbonate. Extraction with chloroform followed by drying of the extract over MgSO$_4$, filtration and evaporation gave a thick gum which crystallised on trituration with n-hexane. Recrystallisation from methanol gave 5,6,7,8-tetrahydroquinoline-8-thiocarboxamide (16g, 30%) m.p. 160°. The hydrochloride was prepared by dissolution of the free base in hot isopropyl alcohol adding ethereal HCl solution and allowing to crystallise. m.p. 263°–4°. (Found: C, 52.6; H, 6.0; N, 12.2. C$_{10}$H$_{12}$N$_2$S, HCl requires C, 52.5; H, 5.7; N, 12.3%).

EXAMPLE 11

4-Methyl-5,6,7,8-tetrahydroquinoline-8-thiocarboxamide hydrochloride

A stirred solution of di-isopropylamine (12.2 ml, 0.085 mol) in benzene (100 ml) at 0° C was treated dropwise with a 9% w/v solution of butyl lithium in hexane (62 ml, 0.085 mol.). After 1 hour at 0° C, 4-methyl-5,6,7,8-tetrahydroquinoline (12.8 g, 0.085 mol) was added dropwise and then after a further hour the anion was treated dropwise with trimethylsilyl isothiocyanate (12.2 ml., 0.095 mol.). After 0.5 hours at 0° C and 0.5 hours at room temperature the solution of 4-methyl-5,6,7,8-tetrahydroquinoline-8-(N-lithio-N-trimethylsilyl)thiocarboxamide was diluted with water (50 ml) causing hydrolysis to 4-methyl-5,6,7,8-tetrahydroquinoline-8-(N-trimethylsilyl)thiocarboxamide and subsequent hydrolysis to the title compound and the pH adjusted to 2.0 with conc. HCl. The aqueous layer was separated and adjusted to pH 10.0 with solid sodium carbonate and extracted with chloroform (3 × 50 ml) and the combined extracts were dried over MgSO$_4$, filtered and the solvent was removed in vacuo. The residual oil was triturated with n-hexane to give 4-methyl-5,6,7,8-tetrahydroquinoline-8-thiocarboxamide (3.4g, 19%). The hydrochloride was prepared by dissolving in hot iso-propyl alcohol adding excess ethereal HCl solution and allowing to crystallise to give 4-methyl-5,6,7,8-tetrahydroquinoline-8-thiocarboxamide, hydrochloride m.p. 212°–3° C. (Found: C, 54.9; H, 6.4; N, 11.5. C$_{11}$H$_{14}$N$_2$S. HCl requires C, 54.4; H, 6.2; N, 11.5%).

EXAMPLE 12

2-Ethyl-5,6,7,8-tetrahydroquinoline-8-thiocarboxamide

By the method described in Example 11, di-isopropylamine (2 ml 0.014 mol) in benzene (20 ml), n-butyl lithium solution (9% w/v, 10 ml, 0.014 mol), 2-ethyl-5,6,7,8-tetrahydroquinoline (2.3 g, 0.014 mol) and trimethylsilyl isothiocyanate (2 ml 0.015 mol) gives 2-ethyl-5,6,7,8-tetrahydroquinoline-8-(N-lithio-N-trimethylsilyl)thiocarboxamide, then 2-ethyl-5,6,7,8-tetrahydroquinoline-8-(N-trimethylsilyl) thiocarboxamide from which was obtained 2-ethyl-5,6,7,8-tetrahydroquinoline-8-thiocarboxamide (600 mg, 20%) m.p. 73°–5° C (Found: C, 63.25; H, 7.6; N, 12.75. C$_{12}$H$_{16}$N$_2$S requires C, 65.4; H, 7.3; N, 12.7%).

EXAMPLE 13

2-Butyl-5,6,7,8-tetrahydroquinoline-8-thiocarboxamide

By the method described in Example 11 using di-isopropylamine (4.45 ml 0.03 mol) in benzene (50 ml), n-butyl lithium solution (9% w/v, 13.5 g, 0.03 mol), 2-butyl-5,6,7,8-tetrahydroquinoline (6 g, 0.03 mol) and trimethylsilyl isothiocyanate (4.45 ml 0.033 mol) gives 2-butyl-5,6,7,8-tetrahydroquinoline-8-(N-lithio-N-trimethylsilyl) thiocarboxamide, then 2-butyl-5,6,7,8-tetrahydroquinoline-8-(N-trimethylsilyl)thiocarboxamide, from which was obtained 2-butyl-5,6,7,8-tetrahydroquinoline-8-thiocarboxamide (1.2 g, 15%) m.p. 54.6° C. (Found: C, 68.0; H, 8.4; N, 11.2. C$_{14}$H$_{20}$N$_2$S requires C, 67.8; H, 8.1; N, 11.3%).

EXAMPLE 14

2-Methyl-4-phenyl-5,6,7,8-tetrahydroquinoline-8-thiocarboxamide

By the method described in Example 11 using di-isopropylamine (11.2 ml. 0.077 mol) in benzene (150 ml), n-butyl lithium solution (9% w/v, 57 ml, 0.077 mol), 2-methyl-4-phenyl-5,6,7,8-tetrahydroquinoline (17.7 g, 0.077 mol), and trimethylsilyl isothiocyanate (11.2 ml. 0.087 mol) gives 2-methyl-4-phenyl-5,6,7,8-tetrahydroquinoline-8-(N-lithio-N-trimethylsilyl)-thiocarboxamide, then 2-methyl-4-phenyl-5,6,7,8-tetrahydroquinoline-8-(N-trimethylsilyl)thiocarboxamide from which was obtained 2-methyl-4-phenyl-5,6,7,8-tetrahydroquinoline-8-thiocarboxamide (1.2 g, 5%) m.p. 174°–5° C. (Found: C, 72.0; H, 6.7; N, 9.4; C$_{17}$H$_{18}$N$_2$S requires C, 72.3; H, 6.4; N, 9.9%).

EXAMPLE 15

3,4-Dimethyl-5,6,7,8-tetrahydroquinoline-8-thiocarboxamide

By the method described in Example 11 using diisopropylamine (4.9 ml. 0.034 mol) in benzene (50 ml), n-butyl lithium solution (9% w/v, 25 ml, 0.034 mol), 3,4-dimethyl-5,6,7,8-tetrahydroquinoline-(5.65g, 0.034 mol) and trimethylsilyl isothiocyanate (4.9 ml, 0.038 mol) gives 3,4-dimethyl-5,6,7,8-tetrahydroquinoline-8-(N-lithio-N-trimethylsilyl)thiocarboxamide, then 3,4-dimethyl-5,6,7,8-tetrahydroquinoline-8-(N-trimethylsilyl)thiocarboxamide from which was obtained 3,4-dimethyl-5,6,7,8-tetrahydroquinoline-8-thiocarboxamide (0.4 g, 5%) m.p. 163°–5° C. (Found: C, 65.1; H, 7.8; N, 12.2. $C_{12}H_{16}N_2S$ requires C, 65.4; H, 7.3; N, 12.2%).

EXAMPLE 16

3-Methyl-5,6,7,8-tetrahydroquinoline-8-thiocarboxamide

To a solution of di-isopropylamine (4.44 g, 0.044 mole) in benzene (30 ml) at 0° C under nitrogen was added with stirring a solution of n-butyl-lithium in hexane (9% w/v, 31.6 ml, 0.044 mole) and the resulting solution was stirred for 1 h at 0° C. 3-Methyl-5,6,7,8-tetrahydroquinoline (5.86 g, 0.04 mole) was added and stirred for a further 1½ h. The reaction mixture was treated with dimethylsilyl di-isothiocyanate (7.66 g, 0.044 mole) and the mixture was stirred for 0.5 h at 0° C and at room temperature for 1 hour. To the solution of 3-methyl-5,6,7,8-tetrahydroquinoline-8-(N-lithio-N-isothiocyanatodimethylsilyl)thiocarboxamide was added water (50 ml) causing hydrolysis to 3-methyl-5,6,7,8-tetrahydroquinoline-8-(N-isothiocyanatodimethylsilyl)thiocarboxamide and subsequent hydrolysis to the title compound, and the pH was adjusted to 2 with conc. HCl. The aqueous layer was separated, washed with ethyl acetate, and the pH was adjusted to 10 with solid sodium carbonate. The resulting mixture was extracted with ethyl acetate (3 × 50 ml.). The combined extracts were dried (MgSO$_4$), filtered, and the solvent was removed in vacuo. The residue was triturated with n-hexane to give 3-methyl-5,6,7,8-tetrahydroquinoline-8-thiocarboxamide (0.9 g, 15%).

Example 17

3-Methyl-5,6,7,8-tetrahydroquinoline-8-thiocarboxamide

A solution of 3-methyl-5,6,7,8-tetrahydroquinoline (1.43 g, 0.01 mole) in benzene (20 ml) was treated with n-butyl-lithium (15% w/w, 4.5 ml, 0.01 mole) and the solution was allowed to stand at room temperature for 0.5 hours. The solution was then treated with a suspension of silicon tetraisothiocyanate (1.3 g, 0.005 mole) in benzene (5 ml) at 0° C. After 10 minutes, water (50 ml.) was added to the solution of 3-methyl-5,6,7,8-tetrahydroquinoline-8-(N-lithio-N-(tri-isothiocyanato) silyl)thiocarboxamide causing hydrolysis to 3-methyl-5,6,7,8-tetrahydroquinoline-8-(N-tri-isothiocyanato)silyl) thiocarboxamide and subsequent hydrolysis to the title compound, and the mixture was stirred for 0.5 h at room temperature and then acidified with conc. HCl. The aqueous layer was separated, washed with ethyl acetate and the pH was adjusted to 10 with solid Na$_2$CO$_3$. The basic mixture was extracted with ethyl acetate (3 × 50 ml) and the combined organic extracts were dried (MgSO$_4$), filtered and evaporated. The residue was triturated with n-hexane to give 3-methyl-5,6,7,8-tetrahydroquinoline-8-thiocarboxamide (0.2 g, 10%).

EXAMPLE 18

5,6,7,8-Tetrahydro-3-methylquinoline-8-(N-triphenylsilyl)thiocarboxamide

A solution of 5,6,7,8-tetrahydro-3-methylquinoline (2.92 g, 20mM) in dry benzene (20 ml) maintained at 0° C under a nitrogen atmosphere was treated with a solution of n-butyl-lithium in hexane (14 ml, 20 mM). After 15 minutes the reaction mixture was treated with a solution of triphenylsilyl isothiocyanate (6.34 g, 20 mM) in benzene (20 ml) then stirred for 1 hour. The reaction mixture was poured onto iced water (100 ml) and the organic layer separated and dried (MgSO$_4$). Evaporation of the solvent under reduced pressure gave an oil which crystallised on trituration with hexane. Recrystallisation of the resulting solid from ethyl acetate/di-isopropyl ether gave the title compound (2.3g, 25%) m.p. 153° C (Found: C, 75.3; H, 6.2; N, 5.65%. $C_{29}H_{28}N_2SSi$ requires: C, 75.0; H, 6.1; N, 6.0%).

EXAMPLE 19

3-Methyl-5,6,7,8-tetrahydroquinoline-8-thiocarboxamide

A solution of 5,6,7,8-tetrahydro-3-methylquinoline-8-(N-triphenylsilyl)thiocarboxamide (2.3g, 5mM) in benzene (50 ml) was stirred with 2N hydrochloric acid (50ml) for 30 minutes. The layers were separate, the aqueous layer basified (pH9) and the product extracted with chloroform (2 × 50 ml).

The organic layer was dried and the solvent removed under pressure to give yellow crystals (800 mg, 78%). The crude title material was converted into the hydrochloride in isopropyl alcohol using ethereal hydrogen chloride. After cooling the resultant crystals were removed by filtration and air dried to give a product identical to authentic 3-methyl-5,6,7,8-tetrahydroquinoline-8-thiocarboxamide hydrochloride. (Found: C, 54.5; H, 6.3; N, 11.4%. $C_{11}H_{14}N_2S \cdot HCl$ requires C, 54.4; H, 6.2; N, 11.5%).

We claim:
1. A compound of formula III

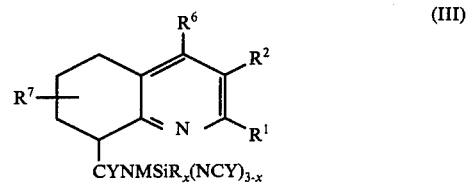

wherein $R^1$, $R^2$ and $R^6$ are independently hydrogen, tri-fluoromethyl, alkyl of 1 to 6 carbon atoms, phenyl alkyl of 7 to 12 carbon atoms or phenyl, or $R^1$ and $R^2$ taken together represent an $R^7$ substituted alkylene chain, said alkylene chain consisting of 3 to 5 carbon atoms, inclusive; $R^7$ is hydrogen, alkyl of 1 to 6 carbon atoms, gem-di-n-alkyl in which each alkyl group has 1 to 6 carbon atoms, phenyl alkyl of 7 to 12 carbon atoms or phenyl; with the proviso that when $R^1$ and $R^2$ or $R^2$ and $R^6$ are both alkyl, they are normal or secondary alkyl; Y is oxygen or sulphur, M is sodium, potassium, lithium, MgCl, MgBr or MgI; each group R is independently alkyl of 1 to 6 carbon atoms, phenyl or phenyl alkyl of 7 to 12 carbon atoms, x is an integer from 0 to 3 inclusive.

2. A compound of formula (IV)

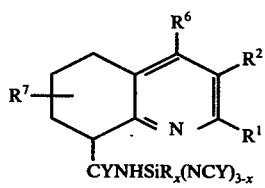
(IV)
wherein $R^1$, $R^2$, $R^6$, $R^7$, Y, R and x are as defined in claim 1.
3. A compound as claimed in claim 2, which is 5,6,7,8-tetrahydro-3-methylquinoline-8-(N-triphenylsilyl)thiocarboxamide.
* * * * *
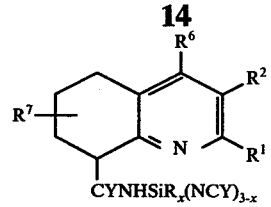
(IV)
wherein $R^1$, $R^2$, $R^6$, $R^7$, Y, R and x are as defined in claim 1.
3. A compound as claimed in claim 2, which is 5,6,7,8-tetrahydro-3-methylquinoline-8-(N-triphenylsilyl)thiocarboxamide.
* * * * *